(12) United States Patent
Kilcher et al.

(10) Patent No.: US 6,576,225 B1
(45) Date of Patent: Jun. 10, 2003

(54) DENTAL CARE COMPOSITION

(75) Inventors: Beat Kilcher, Bosco Luganese (CH);
Patrizia Balmelli, Breganzona (CH);
Gert Silber, Ponte Capriasca (CH);
Beat A. Von Weissenfluh, Gentilino (CH)

(73) Assignee: KerrHawe SA, Bioggio (CH)

( * ) Notice: Subject to any disclaimer, the term of this patent is extended or adjusted under 35 U.S.C. 154(b) by 0 days.

(21) Appl. No.: 09/566,128

(22) Filed: May 5, 2000

(30) Foreign Application Priority Data

May 6, 1999 (EP) .............................. 99810396

(51) Int. Cl.[7] .............................. A61K 7/16; A61K 7/18; A61C 15/00
(52) U.S. Cl. .............................. 424/49; 424/52; 433/216
(58) Field of Search ...................... 424/49, 52; 433/216

(56) References Cited

U.S. PATENT DOCUMENTS

| | | |
|---|---|---|
| 5,124,143 A | 6/1992 | Mühlemann et al. |
| 5,266,304 A * | 11/1993 | Baffelli et al. .................. 424/49 |
| 5,597,553 A | 1/1997 | Baffelli et al. |

FOREIGN PATENT DOCUMENTS

| | | |
|---|---|---|
| WO | WO 9609033 A1 | 3/1996 |
| WO | WO 9609034 A1 | 3/1996 |

* cited by examiner

Primary Examiner—William R. A. Jarvis
Assistant Examiner—Donna Jagoe
(74) Attorney, Agent, or Firm—Wood, Herron & Evans, LLP

(57) ABSTRACT

A dental care composition for the prophylactic dental hygiene (prophylactic paste) comprises as principal components the following: from 10 to 80% by weight, preferably from 35 to 55% by weight, of a polishing body containing plate shaped rock particles, preferably perlite particles; from 20 to 80% by weight, preferably from 40 to 50% by weight, of a nonionic, preferably polymeric surface active agent; and from 0 to 20% by weight, preferably from 1 to 10% by weight, of an emulsifier or emulsifier blend. Polyethylene glycols (Macrogol) having molecular weights of from 200 to 1,000, preferably of from 200 to 600, are particularly suited as pure compounds or as a blend of different variants having different molecular weights. The dental care composition shows a smooth and soft consistency and has only a weak tendency of being splashed during its application in the mouth.

47 Claims, No Drawings

DENTAL CARE COMPOSITION

BACKGROUND OF THE INVENTION

1. Field of the Invention

The present invention is related to a dental care composition to be used for the prophylactic dental hygiene. Such dental care compositions generally include three different types of pastes, classified according to hardness (hard, medium, soft). The structure of these pastes is not comparable to a conventionally used toothpaste and corresponds rather to a nearly crumbly polishing paste. This crumbly structure is necessary when the dentifrice is used in the buccal cavity with a polishing device in order to avoid loss of substances by e.g. splashing. These pastes are used by dental hygienists as a supplement to daily dental care in order to remove stubbornly adhering dental plaque. This additional treatment is intended to support oral hygiene in such a manner that caries are reduced, thus rendering dental treatment almost superfluous.

2. Description of the Prior Art

A water containing paste of such a kind which contains precipitated silicic acid as a major cleaning body component, but also perlite, has been disclosed in EP-A-0,268,763. Another variant which imperatively contains hydrophobic pyrogenic silicic acid as a stabilizer for perlite, is described in EP-A-0,528,756, which is incorporated in the description by reference.

During their application, these dental care compositions, also called prophylactic pastes, show several problems:

The consistence that has a tendency to crumbling renders difficult the taking out from supply or portion recipients and the application onto the dental cleaning tools (paste carriers) of the dental hygienist.

For the same reason, it is impossible to portion the known prophylactic pastes into the preferred amounts for each single application without problems.

Finally, the known prophylactic pastes have the known tendency, when coming into contact with the saliva of the patient, to be mixed with the saliva and to be flung from the paste carrier. These rotating tools are for example working in a speed range of from 2,000 to 6,000 rpm. However, it is often recommended to avoid rotational speeds of more than 3,000 rpm since otherwise the paste flings away from the tool.

The first and major object of the present invention is to provide a dental care composition for the above indicated purpose of prophylactic dental hygiene which has improved application properties. A further object of the invention consists in providing a such paste of improved acceptance by the dental hygienist and the patient. Another object of the invention is to provide a method for the cleaning treatment of teeth in the prophylactic dental hygiene, comprising using a grinding or polishing instrument of the professional dental prophylaxis.

SUMMARY OF THE INVENTION

The objective of the invention is fulfilled by a new dental care composition which contains (A) a cleaning body comprising a major proportion of plate shaped, flat or curved rock particles, (B) an effective amount of at least one nonionic surfactant, and (C) at least one emulsifying agent, the combined amounts of cleaning body (A) and of surfactant (B) being at least 30% by weight of the dental care composition, the proportion of emulsifying agent (C) being comprised between 0 and 20% by weight of the dental care composition.

The method of the invention is characterized by the use of the dental care composition defined in the foregoing paragraph.

Preferred or special embodiments of the present invention will become evident from the following description of the implementation of the invention and from the dependent claims.

The paste according to the invention is thus characterized in that it contains a cleaning or polishing body essentially comprising sharp edged, plate shaped particles of a rock, preferably perlite, and a nonionic surfactant.

The nonionic surfactant fulfills at the same time the function of a solvent. Its nature and amount therefore adjust the flow properties of the dental care composition. It has been found that a polyethylene glycol known under the common name (INN) "Macrogol" which is a polyether, is particularly appropriate. It is believed that the nonionic surfactant forms a kind of hull or shell at least around the rock particles, this hull acting simultaneously as a bonding agent to the remaining free molecules of the surfactant. As a result of these considerations, it can be understood that especially surfactants of moderately long chain have a particularly good effectiveness. Tests have also shown that the use of species of too a long chain will result in a loss of softness of the paste which becomes too "dry" and crumbly. It has furthermore been found that generally the addition of an emulsifyer or an emulsifyer mixture will be required, especially in cases where, in spite of a careful selection of the surfactant, the required softness of the dental care composition cannot perfectly be obtained.

Plate shaped polishing body particles have the tendency of aligning during the cleaning application in such a way that the formation of grooves in the tooth surface and other undesired effects of the action of prophylactic pastes comprising sharp-edged, rather spheroidal particles are significantly reduced. It can thus be expected, starting from these findings, that still other natural or synthetic mineral materials, namely rocks, which are able to be comminuted to plate-shaped particles of appropriate size and shape, may be used instead of the prototype perlite, e.g. bentonite, the zeolithes, vermiculite, pumice stone. The plates may also be curved; perlite particles are shell shaped in the manner of eggshell fragments. A remarkable property of perlite is its ability that its particles will break into pieces during the application but remain nevertheless sharp-edged and conserve their cleaning action in becoming smaller and smaller, analogously to a grinding material turning from a coarse state into increasingly finer ones.

Further details regarding the use of perlite and other rocks in prophylactic pastes can be taken from the published European patent application No. EP-A-0,528,756.

DETAILED DESCRIPTION OF THE INVENTION

The invention shall now be explained in more detail by the description of preferred embodiments thereof. If not other-wise indicated, all percentages in the present document are by weight.

A dental care composition according to the invention comprises at least the following characteristic components:

| | |
|---|---|
| Perlite (expanded) | 10–80% by weight, preferably 35–55% |
| Macrogol | 20–80% by weight, preferably 40–50% |
| Emulsifyer or emulsifier mixture | 0–20% by weight, preferably 1–10% |

| -continued | |
|---|---|
| Additives and active substances | 0–20% by weight, preferably 0–10% |
| Fillers | 0–70% by weight. |

The substance Macrogol is a commercially available product having a defined molecular weight. It assumes as a principal component the function of the otherwise present liquid such as water, and its amount and nature influence the rheology, in particular the viscosity and the softness. The present paste is essentially free from water and other low molecular substances which are liquid at normal temperature (298 K) and usable as solvents such as ethanol, propylene glycol, glycerol, normally present in known dental care compositions. "Low molecular" preferably means in this respect a maximal molecular weight of about 100.

Macrogol species having a molecular weight of from 200 to 1,000, preferably of from 200 to 600, have proven as particularly appropriate. The commercially available products having a narrowly specified average molecular weight range or even those with definite molecular weight may be used alone or in admixture. It is to be expected that a still finer adjustment of the application properties, especially of the rheology, will be obtained by an appropriate blending of surfactants having different molecular weights. For example, when the amount of higher molecular components is increased, a higher viscosity is to be expected.

The perlite which can be used has an average particle diameter of about 30 $\mu$m, 99% thereof being present within the size range of from 1 $\mu$m to 200 $\mu$m.

As an emulsifying agent or emulsifier, the following substances may for example be used: higher fatty alcohols, preferably having from 8 to 20 carbon atoms in the chain which may be saturated or not, e.g., cetyl alcohol, lauryl alcohol, stearyl alcohol; and/or fatty acid ester of a polyoxyethylene, e.g. ethoxylated castor oil (Eumulgin RO40, Henkel KG a.A., Germany) or polyoxyethylene stearate.

The prophylactic paste may further contain one or more of the usually present additives and active agents in the required amounts, preferably from 0% to 10%, namely: antiseptic agent, fluoride salt, flavoring agents, sweetening agent, preserving agent (antioxidant, antimicrobial agent) and optionally additional, secondary abrasive materials. These secondary abrasive bodies constitute the cleaning or polishing body together with the perlite or, generally, the rock.

Fillers may be added to the paste in order to finely adjust its abrasive properties. These fillers must fit in with the requirement that they must not contribute by their own to the abrasive power, i.e. not augment it, and they must not impair the consistency of the paste. Such fillers are accessible to the one skilled in the art by the general technical knowledge. For example, higher molecular polyethylene glycols and wax alcohols may be used as fillers. These higher molecular polyethylene glycols may even be selected from the above described macrogols, where products are to be used as fillers that have higher molecular weights than those above mentioned used as nonionic surfactants.

It has been found in practice that the prophylactic paste which can be manufactured in this manner can be very easily portioned into one-shot doses, has an overall rather creamy consistency compared with the known pastes, and which has nevertheless a weaker tendency to be splashed off from the rotating polishing tool when it comes into contact with saliva. It has been found that the paste is compatible with humidity, i.e. it does not significantly change its application properties in a humid environment and keep it at least during a sufficiently extended time period for remaining effective.

A further advantage of the paste according to the present invention is its pleasant, creamy consistency.

For example, a typical composition of the pastes according to the invention is the following:

EXAMPLE 1

| Component | Amount, % by weight |
|---|---|
| Flavoring agent | 2% |
| Cetyl alcohol | 3% |
| Emulsifier (Eumulgin RO40 from Henkel, Germany) | 3% |
| Coloring agent (red iron oxide) | 1.7% |
| Sodium fluoride | 0.3% |
| Perlite | 45% |
| Polyethylene glycol 400 (Macrogol) | 43% |
| Sweetening agent (Aspartame ®) | 1% |
| Titanium dioxide (pigment) | 2% |

Based upon this description of an embodiment, the one skilled in the art can find variants thereof without leaving the frame of this invention. It may be contemplated to use modified polyethylene glycols or, generally, polyalkylene glycols, e.g. having adequate substituents on the molecular backbone or at the ends thereof, branched chain compounds, esterified or/and etherified derivatives, etc. It may even be thought of polyalkylethers or largely polyethers. Products with other structural elements in the molecular chain may also be contemplated, such as propylene or methylene, as a homopolymer or a copolymer as well. Generally preferred compounds have 1 to 4 carbon atoms per alkylene glycol moiety.

A large range of choice in the adaptation to the application purpose is assumed regarding the selection of the rock and its particle sizes.

The addition of very small amounts of water or other low molecular solvents such as propylene glycol may be contemplated, preferably in a total amount of at most 10% by weight and more preferably of at most 5% by weight in order to optimize the consistency.

The invention has been described in detail with the help of special embodiments. The invention is not limited thereto nor to their variants; it is defined in the appending claims.

What is claimed is:

1. A prophylactic paste dental care composition for the prophylactic dental hygiene, characterized by the fact that it contains
    (A) a cleaning body comprising a major proportion of plate shaped rock particles,
    (B) 20 to 80% by weight of at least one polyethylene glycol nonionic surfactant, and
    (C) at least one emulsifying agent, the combined amounts of cleaning body (A) and of surfactant (B) being at least 30% by weight of the dental care composition, the proportion of emulsifying agent (C) being comprised between 0 and 20% by weight of the dental care composition.

2. The dental care composition according to claim 1, wherein said rock particles are perlite particles.

3. The dental care composition according to claim 2, containing from 10 to 80% by weight of perlite.

4. The dental care composition according to claim 2, containing from 35 to 55% by weight of perlite.

5. The dental care composition according to claim 1, wherein the combined amounts of cleaning body (A) and of surfactant (B) is at least 70% by weight of the dental care composition.

6. The dental care composition according to claim 1, containing from 40 to 50% by weight of the polyethylene glycol, as surfactant (B).

7. The dental care composition according to claim 1, containing from 1 to 10% by weight of emulsifying agent (C).

8. A prophylactic paste dental care composition for the prophylactic dental hygiene, characterized by the fact that it contains
   (A) a cleaning body comprising a major proportion of plate shaped rock particles,
   (B) an effective amount of at least one nonionic surfactant, and
   (C) at least one emulsifying agent, the combined amounts of cleaning body (A) and of surfactant (B) being at least 30% by weight of the dental care composition, the proportion of emulsifying agent (C) being comprised between 0 and 20% by weight of the dental care composition, and
   wherein the dental care composition contains not more than 10% by weight of water and other low molecular substances that have a molecular weight not higher than 100 and are liquid at 298 K.

9. The dental care composition according to claim 8, wherein said nonionic surfactant (B) is a polyether.

10. The dental care composition according to claim 9, wherein said nonionic surfactant (B) is a polyalkyl ether.

11. The dental care composition according to claim 9, wherein said nonionic surfactant (B) is a modified or unmodified polyalkylene glycol.

12. The dental care composition according to claim 11, wherein said polyalkylene glycol comprises alkylene glycol groups having from 1 to 4 carbon atoms.

13. The dental care composition according to claim 11, wherein said polyalkylene glycol comprises essentially ethylene glycol groups only.

14. The dental care composition according to claim 8, wherein said surfactant consists essentially of molecules having a molecular weight within the range of from 200 to 1,000.

15. The dental care composition according to claim 14, wherein said surfactant consists essentially of molecules having a molecular weight within the range of from 200 to 600.

16. The dental care composition according to claim 8, containing not more than 5% by weight of water and other low molecular substances that have a molecular weight not higher than 100 and are liquid at 298 K.

17. The dental care composition according to claim 8, further containing at least one of the following substances as additional components:
   antiseptic agent,
   fluoride salt,
   flavoring agent,
   sweetening agent,
   preserving agent such as antibiotic agent,
   antioxidizing agent and
   at least one secondary abrasive material in said cleaning body.

18. The dental care composition according to claim 17, wherein the total amount of the additional components is not higher than 20% by weight.

19. The dental care composition according to claim 17, wherein the total amount of the additional components is comprised between 0 and 10% by weight.

20. The dental care composition according to claim 8, containing from 1 to 10% by weight of emulsifying agent (C).

21. The dental care composition according to claim 8, further comprising from 0 to 70% by weight of at least one filler for adjusting the abrasive power of the dental care composition, this filler being selected such that neither the consistency of the dental care composition is impaired nor the filler material provides an abrasive effect of its own.

22. The dental care composition according to claim 8, wherein said rock particles are perlite particles.

23. The dental care composition according to claim 22, containing from 10 to 80% by weight of perlite.

24. The dental care composition according to claim 22, containing from 35 to 55% by weight of perlite.

25. The dental care composition according to claim 8, wherein the combined amounts of cleaning body (A) and of surfactant (B) is at least 70% by weight of the dental care composition.

26. The dental care composition according to claim 8, containing from 20 to 80% by weight of a polyethylene glycol, as surfactant (B).

27. A prophylactic paste dental care composition for the prophylactic dental hygiene, characterized by the fact that it contains
   (A) a cleaning body comprising a major proportion of plate shaped rock particles,
   (B) an effective amount of at least one nonionic surfactant, and
   (C) at least one emulsifying agent selected from a group comprising higher fatty alcohols, fatty acid esters of polyalkyl ethers, and polyoxyethylene stearate, the combined amounts of cleaning body (A) and of surfactant (B) being at least 30% by weight of the dental care composition, the proportion of emulsifying agent (C) being comprised between 0 and 20% by weight of the dental care composition.

28. The dental care composition of claim 27, being essentially free from water and other low molecular substances that have a molecular weight not higher than 100 and are liquid at 298 K.

29. The dental care composition according to claim 27, wherein said higher fatty alcohols are selected from a group comprising compounds having from 8 to 20 carbon atoms in the hydrocarbon backbone, cetyl alcohol, stearyl alcohol, and lauryl alcohol.

30. The dental care composition according to claim 27, wherein said fatty acid esters of polyalkyl ethers comprise ethoxylated castor oil.

31. The dental care composition according to claim 27, containing from 20 to 80% by weight of a polyethylene glycol, as surfactant (B).

32. The dental care composition according to claim 27, wherein said surfactant consists essentially of molecules having a molecular weight within the range of from 200 to 1,000.

33. The dental care composition according to claim 27, further containing not more than 10% by weight of water and other low molecular substances that have a molecular weight not higher than 100 and are liquid at 298.

34. A method for the cleaning treatment of teeth in the prophylactic dental hygiene, comprising using together with a grinding or polishing instrument of the professional dental prophylaxis, a prophylactic paste dental care composition containing (A) a cleaning body comprising a major proportion of plate shaped rock particles, (B) an effective amount of at least one nonionic surfactant, and (C) at least one emulsifying agent, the combined amounts of cleaning body (A) and of surfactant (B) being at least 30% by weight of the dental care composition, the proportion of emulsifying agent (C) being comprised between 0 and 20% by weight of the dental care composition, and the prophylactic paste dental care composition having not more than 10% by weight of water and other low molecular substances that have a molecular weight not higher than 100 and are liquid at 298 K.

35. A prophylactic paste dental care composition for the prophylactic dental hygiene, comprising:

(A) a cleaning body comprising a major proportion of plate shaped rock particles, (B) an effective amount of at least one nonionic surfactant, and (C) at least one emulsifying agent, wherein the combined amount of cleaning body (A) and surfactant (B) is at least 30% by weight of the dental care composition, and the amount of emulsifying agent (C) is between 0 and 20% by weight of the dental care composition, and wherein the dental care composition is essentially free from water and other low molecular substances that have a molecular weight not higher than 100.

36. The dental care composition according to claim 35, wherein said rock particles are perlite particles.

37. The dental care composition according to claim 36, wherein the combined amounts of cleaning body (A) and of surfactant (B) is at least 70% by weight of the dental care composition.

38. The dental care composition according to claim 36, containing from 10 to 80% by weight of perlite.

39. The dental care composition according to claim 35, containing from 20 to 80% by weight of a polyethylene glycol, as surfactant (B).

40. The dental care composition according to claim 39, containing from 40 to 50% by weight of the polyethylene glycol, as surfactant (B).

41. A prophylactic paste dental care composition for the prophylactic dental hygiene, comprising:

(A) a cleaning body comprising a major proportion of plate shaped rock particles, (B) an effective amount of at least one nonionic surfactant having a molecular weight of at least 200, and (C) at least one emulsifying agent, wherein the combined amount of cleaning body (A) and surfactant (B) is at least 30% by weight of the dental care composition, and the amount of emulsifying agent (C) is between 0 and 20% by weight of the dental care composition.

42. The dental care composition according to claim 41, wherein said rock particles are perlite particles.

43. The dental care composition according to claim 42, wherein the combined amounts of cleaning body (A) and of surfactant (B) is at least 70% by weight of the dental care composition.

44. The dental care composition according to claim 42, containing from 10 to 80% by weight of perlite.

45. The dental care composition according to claim 41, containing from 20 to 80% by weight of a polyethylene glycol, as surfactant (B).

46. The dental care composition according to claim 45, containing from 40 to 50% by weight of the polyethylene glycol, as surfactant (B).

47. A prophylactic paste dental care composition for the prophylactic dental hygiene, comprising:

(A) 35–55% by weight of plate shaped perlite particles, (B) at least 20% by weight of polyethylene glycol nonionic surfactant, and (C) up to 20% by weight of an emulsifying agent.

* * * * *

UNITED STATES PATENT AND TRADEMARK OFFICE
CERTIFICATE OF CORRECTION

PATENT NO. : 6,576,225 B1
DATED : June 10, 2003
INVENTOR(S) : Kilcher et al.

It is certified that error appears in the above-identified patent and that said Letters Patent is hereby corrected as shown below:

Column 2,
Line 22, reads "too a long chain" and should read -- too long a chain --.

Column 6,
Line 65, reads "at 298." and should read -- at 298 K. --.

Signed and Sealed this

Eleventh Day of November, 2003

JAMES E. ROGAN
*Director of the United States Patent and Trademark Office*